United States Patent
Cartmell et al.

(10) Patent No.: US 6,276,054 B1
(45) Date of Patent: *Aug. 21, 2001

(54) METHOD OF MANUFACTURING A DISPOSABLE ELECTRODE

(75) Inventors: James Vernon Cartmell, Xenia; Wayne Robert Sturtevant, Centerville; Michael Lee Wolf, West Milton, all of OH (US)

(73) Assignee: NDM, Inc., Dayton, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/207,181

(22) Filed: Dec. 8, 1998

Related U.S. Application Data

(62) Division of application No. 08/866,847, filed on May 30, 1997.

(51) Int. Cl.[7] .................................................. H01R 43/00
(52) U.S. Cl. ........................... 29/825; 29/884; 156/252; 156/292; 600/392; 607/149; 607/152
(58) Field of Search ............................ 29/825, 884, 877; 53/450, 461; 128/641; 156/226, 252, 291–293; 600/391, 392; 607/149, 152, 153

(56) References Cited

U.S. PATENT DOCUMENTS

| | | |
|---|---|---|
| 3,976,055 | 8/1976 | Monter et al. . |
| 4,051,842 | 10/1977 | Hazel et al. . |
| 4,063,352 * | 12/1977 | Bevilacqua ..................... 29/884 |
| 4,166,453 | 9/1979 | McClelland . |
| 4,178,052 | 12/1979 | Ekbom et al. . |
| 4,239,046 | 12/1980 | Ong . |
| 4,257,424 | 3/1981 | Cartmell . |
| 4,268,101 | 5/1981 | Stone . |
| 4,319,579 | 3/1982 | Cartmell . |
| 4,350,165 | 9/1982 | Striese . |
| 4,353,372 | 10/1982 | Ayer . |
| 4,367,755 | 1/1983 | Bailey . |
| 4,409,981 * | 10/1983 | Lundberg ..................... 29/825 X |
| 4,458,696 | 7/1984 | Larimore . |
| 4,635,642 | 1/1987 | Cartmell et al. . |
| 4,643,193 | 2/1987 | DeMarzo . |
| 4,653,501 | 3/1987 | Cartmell et al. . |
| 4,674,511 | 6/1987 | Cartmell . |
| 4,699,679 | 10/1987 | Cartmell et al. . |
| 4,721,111 | 1/1988 | Muttitt . |
| 4,727,881 | 3/1988 | Craighead et al. . |
| 4,763,660 | 8/1988 | Kroll et al. . |
| 4,773,424 | 9/1988 | Inoue et al. . |
| 4,797,125 | 1/1989 | Malana . |
| 4,827,939 | 5/1989 | Cartmell et al. . |
| 4,945,911 | 8/1990 | Cohen et al. . |
| 5,160,328 | 11/1992 | Cartmell et al. . |
| 5,195,523 | 3/1993 | Cartmell et al. . |

(List continued on next page.)

FOREIGN PATENT DOCUMENTS

| | | |
|---|---|---|
| 0029297 | 5/1981 | (EP) . |
| 0 194 823 A2 | 9/1986 | (EP) . |
| 0217383 | 4/1987 | (EP) . |
| WO 94/07409 | 4/1994 | (WO) . |
| WO 96/01077 | 1/1996 | (WO) . |

*Primary Examiner*—Lee Young
*Assistant Examiner*—Rick Kiltae Chang
(74) *Attorney, Agent, or Firm*—Killworth, Gottman, Hagan & Schaeff LLP

(57) ABSTRACT

A biomedical electrode for an electrocardiograph or similar device is provided. The biomedical electrode includes a disposable electrode having an electrically conductive gel layer and a reusable leadwire adapter having the relatively expensive metallic conductive material. The disposable electrode interfaces with the reusable leadwire adapter through the adhesive characteristics of the gel layer. The reusable leadwire includes a stud member which snaps into a standard leadwire connector.

17 Claims, 4 Drawing Sheets

U.S. PATENT DOCUMENTS

| | | |
|---|---|---|
| 5,402,780 | 4/1995 | Faasse, Jr. . |
| 5,406,945 | 4/1995 | Riazzi et al. . |
| 5,429,589 | 7/1995 | Cartmell et al. . |
| 5,476,443 | 12/1995 | Cartmell et al. . |
| 5,501,661 | 3/1996 | Cartmell et al. . |
| 5,511,549 * | 4/1996 | Riazzi et al. .......................... 128/641 |
| 5,632,274 | 5/1997 | Quedens et al. . |
| 5,881,538 * | 3/1999 | Blohm .................................. 53/461 |

* cited by examiner

METHOD OF MANUFACTURING A DISPOSABLE ELECTRODE

CROSS-REFERENCE TO RELATED APPLICATION

This is a divisional application of co-pending application Ser. No. 08/866,847 filed on May 30, 1997 by Cartmell et al., entitled BIOMEDICAL ELECTRODE HAVING A DISPOSABLE ELECTRODE AND A REUSABLE LEADWIRE ADAPTER THAT INTERFACES WITH A STANDARD LEADWIRE CONNECTOR.

BACKGROUND OF THE INVENTION

The invention relates to the field of disposable biomedical electrodes for establishing an electrical connection between the skin of the human anatomy and an electromedical apparatus. More specifically, the present invention relates to a disposable biomedical electrode used in conjunction with a reusable leadwire adapter for an electrocardiograph or similar monitoring equipment.

Medical electrodes of the foregoing type are utilized in a number of applications for a variety of purposes. The monitoring of physiological electric potentials to detect muscular activity of the heart muscle is generally well established, such apparatus being referred to in the art as electrocardiograph (also referred to herein as ECG) apparatus. The resulting traces derived from such apparatus provide a diagnostic tool for detecting heart disease and defects. Such monitoring of physiological electrical potentials may be employed in a number of other applications. However, the disposable biomedical electrode and reusable leadwire adapter of the present invention will be described herein with reference to their connection with ECG apparatus.

Such ECG traces may be desired in a number of different situations. For example, a simple ECG test to obtain a single tracing for diagnostic purposes may be carried out in a few minutes in a physician's office. Hence, medical electrodes utilized for such testing may be of a relatively simple disposable variety, since they are only in service for a very short time. Conversely, longer term monitoring applications require that the medical electrodes remain in place on the patient's skin for considerably extended periods of time. For example, in stress testing, the heart activity of the patient is monitored over a relatively longer period of time while the patient exercises on a tread mill or similar apparatus. Such testing may include monitoring of the heart activity during the exercise, as well as continued monitoring during the rest period thereafter so as to monitor the return of the heart to a normal or unstressed condition. Similarly, medical electrodes monitoring heart activity during surgery may be required to remain in place and operational for a period of several hours. In a similar fashion, patients hospitalized in an intensive care ward or other specialized care unit may require continuous, extended monitoring. Hence, medical electrodes utilized for long term ECG monitoring may be required to remain in service for many hours, and sometimes for many days.

Accordingly, there is a continuing need for high quality yet inexpensive medical electrodes for ECG and related uses which reliably transmit signals to enable traces to be obtained that accurately represent signals generated by the patient's heart. For purposes of convenience and safety, such medical electrodes should be inexpensive so that it is practical to dispose of them after only one use. In the past, an approach to providing inexpensive ECG medical electrodes has been to provide a disposable medical electrode which includes an electrolyte and a conductor engaged therein. For example, U.S. Pat. Nos. 4,773,424, 4,257,424, 4,643,193, 4,721,111 and 4,727,881 are all directed to disposable medical electrodes having an electrolyte and a conductor engaged therein.

It is generally recognized that, in order to obtain high quality traces, the portion of the electrode conductor engaged in the electrolyte should be a conductive material. A biomedical electrode may include a first electrical conductor that is galvanically inactive in the presence of the electrolyte and a second electrical conductor that is galvanically active in the presence of the electrolyte. The second electrical conductor may consist of a minute particle of conductive material located at the interface between the first electrical conductor and the electrolyte. The minute particle of conductive material at the interface can be practically any metal that is galvanically active in the presence of the electrolyte. The metals or metal compounds present at the interface are preferably substantially pure. For example, U.S. Pat. No. 3,976,055, herein incorporated by reference, teaches that the galvanically active material may consist of numerous different types of metals and may be applied to the first electrical conductor by varying methods and quantities.

It is preferable that the conductive material in a biomedical electrode consist of either silver or a silver coated conductive plastic. When pure metallic silver is used, the electrolyte will preferably contain a chloride ion, thus forming a conductor coating commonly referred to in the art as a silver/silver chloride system. Such silver/silver chloride systems provide a regular electrocardiograph trace having a stable base line. The silver/silver chloride system eliminates the erratic traces and wandering base lines sometimes attributed to defibrillation. However, the silver/silver chloride part of the electrode is extremely expensive when compared to the costs associated with the other components of the medical electrode. There have been many attempts in the past to minimize the expense associated with silver/silver chloride systems used in medical electrodes. For example, U.S. Pat. No. 4,674,511 (commonly assigned) discloses a medical electrode for ECG monitoring which includes a conductor member comprising a thin strip of nonconductive material having a thin layer of electrically conductive paintable material adhered to one face thereof. By including only a thin strip of electrically conductive material on the medical electrode, the expense associated with such electrically conductive materials is minimized. However, the disposable medical electrode disclosed in U.S. Pat. No. 4,674,511 does in fact include the expensive electrically conductive material as a component and therefore, is discarded with the medical electrode. The disposition of the electrically conductive material increases the expense of using the disposable medical electrode.

As a response to such problems, attempts in the art have sought to provide a medical electrode having a reusable conductor portion. These medical electrodes typically comprise a disposable portion and a reusable conductor portion. For example, U.S. Pat. No. 4,653,501 (commonly assigned) discloses a medical electrode with a reusable conductor comprising a disposable electrode pad with a socket for receiving a reusable electrode conductor which is attached to a leadwire. The pad includes a socket plate having a release coated lower surface and a bore filled with a gel matrix which serves as the electrolyte contacting the patient's skin. In use, the medical electrode is applied to the skin of the patient and the releasable part of the clamp plates is peeled away from the socket plate. The electrode conductor is then inserted into the bore of the socket plate and the clamp is readhered to the socket plate in a covering relationship. The leadwire is then attached to the end such that the end of the leadwire and the electrode conductor are securely held in place relative to the electrolyte gel matrix.

Another attempt to minimize the expense of the medical electrode by incorporating a reusable conductor is disclosed in U.S. Pat. No. 4,635,642 (commonly assigned). The medical electrode comprises an electrode pad provided with a socket and a reusable electrode conductor which is attached to a leadwire. The electrode pad includes a laminated assembly of a pair of foamed sheets with an electrolyte gel matrix filling the gap between the foam sheets. An electrically nonconductive socket plate is disposed over the gel matrix and the foam sheets. The socket plate is provided with a socket or bore for receiving the reusable electrode conductor. The reusable electrode conductor has a ridged body slightly larger than the bore such that the bore resiliently engages the conductor. While these medical electrode assemblies may incorporate a reusable conductor, they are relatively expensive to manufacture in view of their complex structure as compared to other medical electrodes. Accordingly, medical electrodes having reusable conductors require a relatively sophisticated manufacturing scheme which significantly increases the cost of each medical electrode. Such costs substantially negate any savings associated with the reusable conductor feature.

Further, medical electrodes having reusable conductors in the prior art require non-standardized leadwires. Most hospitals and health care providers are equipped with standard leadwires which comprise a female portion of a snap fastener. The disposable electrode comprises the male portion of the snap fastener which snaps into the female portion of the standard leadwire. Non-standardized leadwires necessitate complete conversion within a hospital which is extremely difficult and expensive.

Accordingly, there remains a need in the art for a reusable leadwire adapter which is adaptable to standard leadwires; there is also a need for a disposable biomedical electrode assembly having a simple structure which is relatively inexpensive to manufacture; there is also a need for a biomedical electrode assembly which eliminates the expensive metallic conductive materials from the disposable portion of the biomedical electrode assembly so as to decrease the costs associated with use.

SUMMARY OF THE INVENTION

The present invention meets the aforementioned needs by providing a biomedical electrode requiring less expensive materials and which may be inexpensively manufactured. The biomedical electrode according to the present invention is used to interconnect a standard leadwire connector to a patient. The biomedical electrode comprises a disposable electrode and a reusable leadwire adapter. The disposable electrode is secured to the skin of a patient and serves to conduct the electrical signal between the patient and the reusable leadwire adapter. The reusable leadwire adapter has several functions. For example, the reusable leadwire adapter serves as the electrode sensor or conductor and as the interface between the disposable electrode and the standard leadwire connector. Additionally, the reusable leadwire adapter houses the electrode sensor or conductor. The combination of the disposable electrode and the reusable leadwire electrode, defined herein as the biomedical electrode, performs the medical electrode function of serving as a transducer between ionic and electric current flow. In this way, the reusable leadwire adapter is attached to the disposable electrode to provide a conductive path for the minute voltages generated by the patient's heart to the ECG apparatus. The biomedical electrode of the present invention provides a regular trace having a stable base line.

According to an aspect of the present invention, a disposable electrode comprises a first layer of material having a first surface and a second surface with an adhesive coating for adhesion to the skin of a patient. The disposable electrode also defines at least one opening. An electronically conductive gel layer is mounted on the first surface of the first layer and covers the at least one opening such that the gel layer contacts the skin of the patient through the opening when the electrode is applied to the skin of the patient.

The disposable electrode further comprises a support layer disposed within the electrically conductive gel layer and coextensive therewith. The disposable electrode may comprise an electrical stabilizing strip coupled to the electrically conductive gel layer and extending across the opening such that direct contact between the gel layer and the skin of the patient is prevented in a portion of the opening. A width of the electrical stabilizing strip is less than a width of the electrically conductive gel layer and a width of the at least one opening. The electrical stabilizing strip comprises an insulating material, such as a polyester material. The electrically conductive gel layer may comprise a hydrogel material while the first layer of material is formed of a porous material having sufficient porosity such that the electrically conductive gel layer adheres to the first layer.

The disposable electrode may further comprise a release liner for protection of the disposable electrode prior to use. The release liner is secured to and covers the second surface of the first layer of material. The release liner may cover both of the first and second surfaces of the first layer of material. The disposable electrode may further comprise a pull tab coupled to the second surface of the first layer of material, so as to provide a surface which is free of the adhesive coating to facilitate removal of the electrode from the release liner. The first layer of material may comprise a grippable portion to facilitate handling and positioning of the electrode. The adhesive coating may extend substantially over the entire second surface of the first layer.

According to another aspect of the present invention, a biomedical electrode for use with a standard leadwire connector comprises a reusable leadwire adapter which is reusable and which interfaces with the standard leadwire connector, and a disposable electrode which is discarded after each use and which interfaces with the reusable leadwire adapter and a patient. The disposable electrode comprises an electrically conductive gel layer which directly engages the reusable leadwire adapter.

The reusable leadwire adapter comprises a mounting layer of material having a first surface and a second surface interfacing with the electrically conductive gel layer. The reusable leadwire adapter also defines a first opening. The reusable leadwire adapter also includes an electrically conductive terminal having a base portion integrally joined to a stud member. The base portion is mounted to the first surface of the mounting layer over the first opening with the stud member sized to interface with the standard leadwire connector. The electrically conductive terminal further includes an electrically conductive eyelet mounted on the second surface of the mounting layer over the first opening and electrically coupled to the conductive terminal. The conductive terminal may comprise a metallic material, such as stainless steel. The conductive eyelet comprises at least one metallic particle, such as silver which may also be chlorinated. The conductive eyelet may further comprise plastic material. The mounting layer may comprise a polyurethane material.

The disposable electrode further comprises a support layer disposed within the electrically conductive gel layer and coextensive therewith. The disposable electrode may comprise an electrical stabilizing strip coupled to the electrically conductive gel layer and extending across the opening such that direct contact between the gel layer and the skin of the patient is prevented in a portion of the opening. A width of the electrical stabilizing strip is less than a width of the electrically conductive gel layer and a width of the at least one opening. A width of the electrical stabilizing strip is substantially equal to a width of the conductive eyelet. The electrical stabilizing strip comprises an insulating material, such as a polyester material. The electrically conductive gel layer amy comprise a hydrogel material while the first layer of material is formed of a porous material having sufficient porosity such that the electrically conductive gel layer adheres to the first layer.

The disposable electrode may further comprise a release liner for protection of the disposable electrode prior to use. The release liner is secured to and covers the second surface of the first layer of material. The release liner may cover both of the first and second surfaces of the first layer of material. The disposable electrode may further comprise a pull tab coupled to the second surface of the first layer of material, so as to provide a surface which is free of the adhesive coating to facilitate removal of the electrode from the release liner. The first layer of material may comprise a grippable portion to facilitate handling and positioning of the electrode. The adhesive coating may extend substantially over the entire second surface of the first layer.

According to yet another aspect of the present invention, a method of manufacturing disposable electrodes comprises providing a first layer of material having a first surface and a second surface. An adhesive is applied to the second surface of the first layer. Openings are formed through the first layer at predetermined intervals. An electrically conductive gel web is applied to the first surface of the first layer, such that the gel web extends over all of the openings.

The first layer of material may be cut to a desired shape. A release liner may be applied to the first layer. The release liner may be applied to the second surface of the first layer and then folded over the first surface of the first layer. A separation cut may be made through the first layer of material between adjacent disposable electrodes. A covering may be applied over a portion of the second surface of the first layer, so as to provide a grippable surface to facilitate removal of the disposable electrode from the release liner. An electrical stabilizing strip may be applied to the electrically conductive gel web. The electrical stabilizing strip may comprises an insulating material, such as a polyester material. The electrically conductive gel web may comprises a hydrogel while the first layer may be formed of a porous material having sufficient porosity such that the first layer is laminated on the electrically conductive gel web. The electrically conductive gel web may comprise a support layer disposed within the electrically conductive gel web.

A major portion of the cost savings arise by virtue of the reusable lead wire connector including as a component the relatively expensive metallic conductive material. In the past, the disposable portion of the electrode included the metallic conductive material such as the silver/silver chloride system, which was discarded after a single use. This significantly added to the cost of using each electrode. Past attempts in the art have incorporated the conductive material in a reusable nonstandard leadwire connector. However, hospitals and health care providers have been reluctant to replace standard leadwire connectors. The present invention provides a solution by incorporating the conductive material in a reusable leadwire adapter which interfaces with a standard leadwire connector, thereby eliminating the expensive metallic conductive material from disposable portion of the electrode. Other objects and advantages of the invention will be apparent from the following description, the accompanying drawings and the appended claims.

Note: All figures are illustrative and are not drawn to scale.

DETAILED DESCRIPTION OF THE PREFERRED EMBODIMENTS

Figure 1:
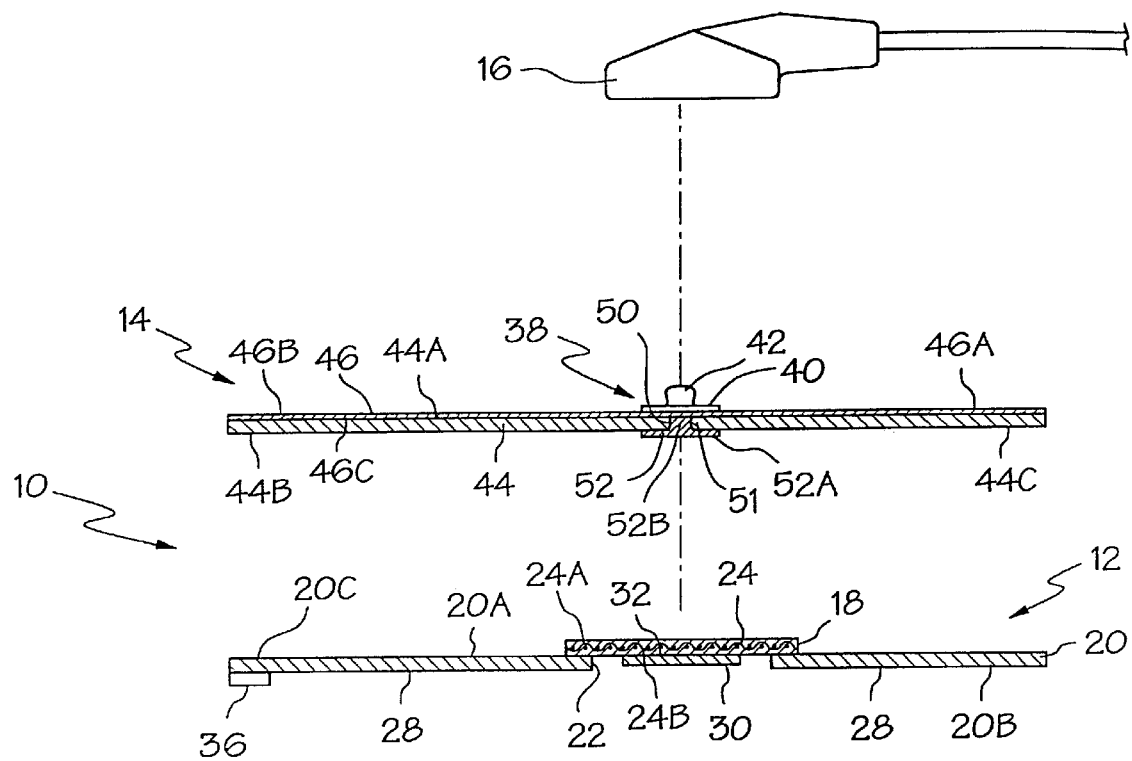
FIG. 1 is a schematic view of a biomedical electrode in accordance with an embodiment of the present invention.

Referring now to FIG. 1, a biomedical electrode 10 which comprises a disposable electrode 12 and a reusable leadwire adapter 14 is shown in accordance with an embodiment of the present invention. The disposable electrode 12 will be discarded after a single use while the reusable leadwire adapter 14 will be used repeatedly. The disposable electrode 12 may be secured directly to the skin of a patient requiring ECG monitoring. The reusable leadwire adapter 14 interfaces with a standard leadwire connector 16 and the disposable electrode 12. The standard leadwire connector 16 is used by most hospitals and health care providers. The standard leadwire connector 16 comprises the female portion of a snap connector (not shown). The standard leadwire connector 16 snaps onto a correspondingly configured male portion of a snap connector and transmits generated ECG signals to a processing device (not shown) for display and interpretation.

Figure 2:
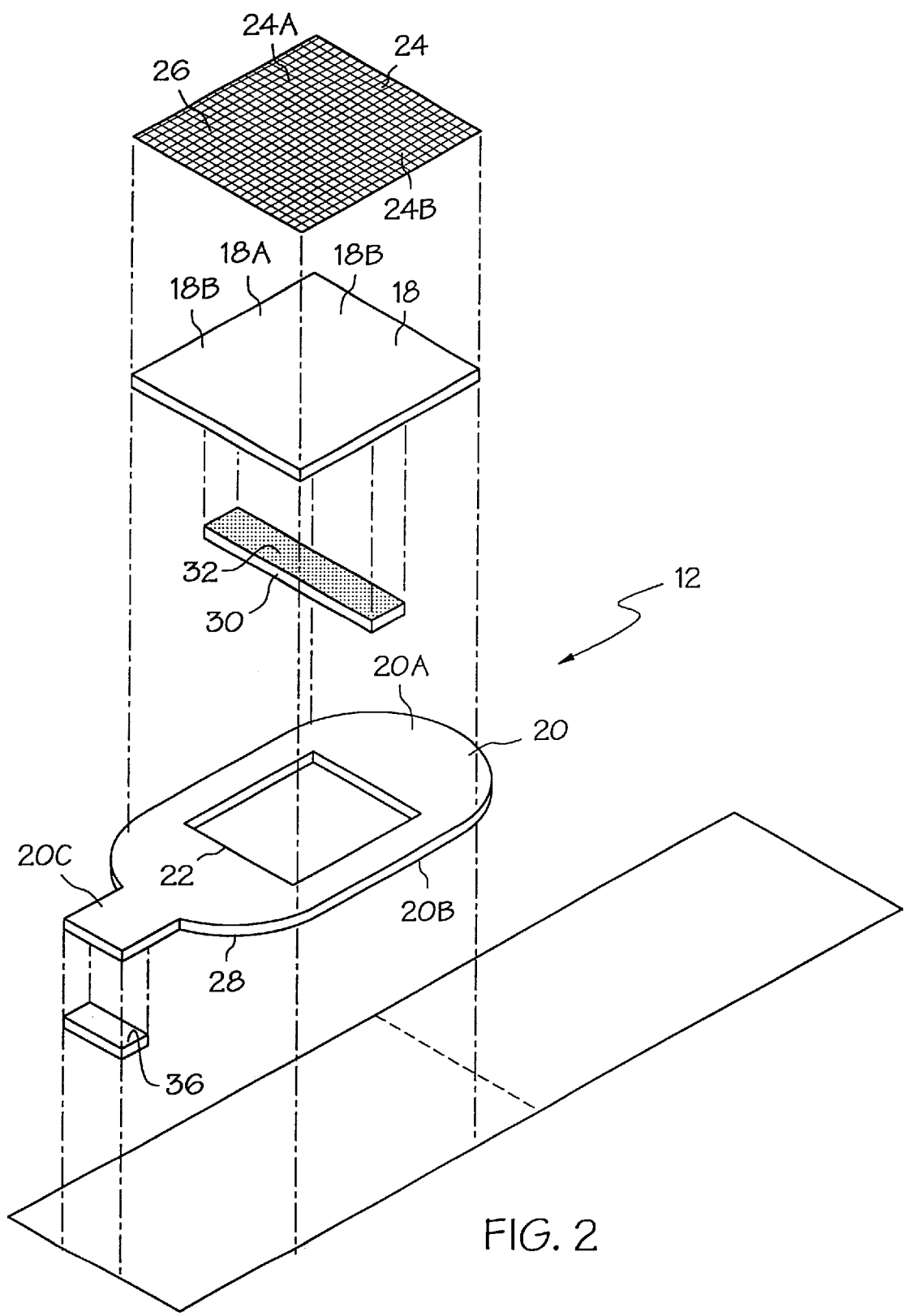
FIG. 2 is an exploded view of the disposable electrode in accordance with an embodiment of the present invention.

Referring to FIGS. 1 and 2, the disposable electrode 12 does not include any metallic conductive material. Rather, the disposable electrode 12 comprises an electrically conductive gel layer 18 coupled to a first or upper surface or side 20A of a first layer of material 20 having at least one opening 22. The first layer 20 is formed of a porous material having sufficient porosity such that the first layer 20 can be secured or laminated to the gel layer 18 without an adhesive. The gel layer 18 extends sufficiently over the opening 22 so that it is adequately secured or laminated to the first layer 20. It has been found that when the first layer 20 is formed of sufficiently porous material, it readily adheres to most conventional electrically conductive gels, such as electrolytic gels and hydrogels. Other materials may not adhere as readily to electrolytic gels, such as hydrogels, and, thus, require an adhesive coating in order to provide a means by which the first layer 20 can be secured to the gel layer 18.

Preferably, the first layer of material 20 is formed of a porous material comprising a foam material including silica and a polyoelfin, wherein the porous material has a porosity ranging from about 30% to about 80%. The preferred porous material is a microporous synthetic sheet commercially available from PPG Industries, Inc. under the trademark Teslin®. Those skilled in the art will understand that the extent to which the porous material must be porous will depend upon the particular gel material chosen to form the gel layer 18. Further, those skilled in the art will appreciate that sufficiently porous materials other than those described herein may be used without departing from the scope of the invention. Finally, those skilled in the art will appreciate that the degree to which the gel material permeates the first layer 20 will depend on the materials chosen and the porosity of the first layer 20. In the illustrated embodiment, the first surface 20A of the first layer 20 may be printed to improve the esthetics of the first layer 20.

Further, the disposable electrode 12 may also include an optional support structure or scrim 24 which is coextensive with the gel layer 18. The support structure 24 adds additional support to the gel layer 18 and facilitates handling of the gel layer 18 during processing. The support structure 24 is composed of a permeable material, such as woven and nonwoven fabrics, gauze, scrim, or other similar materials. The permeable fabric of the support structure 24 contains interstices 26 which allow the gel layer 18 to pass through the support structure 24, resulting in the presence of the gel layer 18 on both a first surface 24A and a second surface 24B of the support structure 24.

A second or lower surface or side 20B of the first layer 20 includes a patient-contact adhesive coating 28. The patient-contact adhesive coating 28 comprises a pressure sensitive adhesive which extends substantially over the entire second surface 20B of the first layer 20. The adhesive coating 28 is used to secure the second surface 20A of the first layer 20, and hence, the disposable electrode 12 to the skin of the patient.

In the illustrated embodiment, the first layer 20 is oblong shaped with a grippable portion 20C. The grippable portion 20C is sized so that the disposable electrode 12 may be easily grasped with two fingers to facilitate handling and positioning of the electrode 12. The first layer 20 is sized to provide sufficient contact between the disposable electrode 12 and the patient's skin. Further, the opening 22 is rectangular shaped and positioned substantially in the center of the first layer 20. The opening 22 and the gel layer 18 are sized to provide good electrical and physical contact between the gel layer 18 and the reusable leadwire adapter 14. It will be appreciated by those skilled in the art that the first layer 20 may have any shape that is compatible with the patient and the reusable leadwire adapter 14. For example, the first layer 20 may also be circular, oval, square or rectangular. It will be further appreciated by those skilled in the art that the opening 22 may have any appropriate size and shape to provide sufficient contact between the gel layer 18 and the reusable leadwire adapter 14, and good electrical contact between the gel layer 18 and the patient's skin.

Additionally, the disposable electrode 12 may comprise an electrical stabilizing strip 30. In the illustrated embodiment, the upper surface or side of the electrical stabilizing strip 30 includes an adhesive 32. The electrical stabilizing strip 30 is adhesively mounted to a second or lower surface or side of the electrically conductive gel layer 18. The electrical stabilizing strip 30 is positioned over a center portion 18A of the gel layer 18 and has a width which is less than a width of the gel layer 18, such that the gel layer 18 makes contact with the patient through an outer portion 18B of the gel layer 18. The width of the electrical stabilizing strip 30 is also less than a width of the opening 22. The electrical stabilizing strip 30 is comprised of an insulating material, such as polyester.

Figure 3:
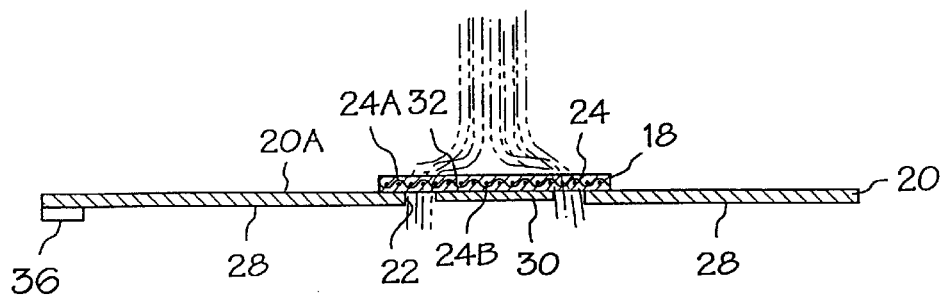
FIG. 3 is a side view of the disposable electrode illustrating the signal blocking function of the electrical stabilizing strip.

The electrical stabilizing strip 30 blocks direct electrical contact between the patient's skin and the reusable leadwire adapter 14. Blocking direct electrical contact reduces the noise that is produced when the patient moves or when a nurse adjusts the disposable electrode 12. All signals are forced to travel around the electrical stabilizing strip 30, as shown in FIG. 3, through at least some portion of the gel layer 18. Any shifting of the disposable electrode 12 caused by patient movement will have a minimal effect on any generated signals since the signals must travel around the electrical stabilizing strip 30 to the reusable leadwire adapter 14. The electrical stabilizing strip 30 is important for electrodes used for long term monitoring and stress testing since the patient is physically active. The effects of noise caused by patient movement can be reduced leading to higher quality traces.

As shown in FIG. 2, the disposable electrode 12 further includes a release liner 34. The release liner 34 covers the first and second surfaces 20A, 20B of the first layer 20 to protect the disposable electrode 12 prior to use. The release liner 34 helps prevent the gel layer 18 from drying out and prevents contamination of the patient-adhesive coating 28 and the gel layer 18. An optional pull tab 36 may be secured to the grippable portion 20C of the first layer 20. The pull tab 36 provides a surface which is free of the patient-adhesive coating 28 so that the disposable electrode 12 may be handle without contacting the coating 28. When the pull tab 36 is used in conjunction with the release liner 34, the user can simply peel the disposable electrode 12 away from the liner 34 by grasping the grippable portion 20C along the pull tab 36. Thereafter, the user can remove the pull tab 36 and mount the disposable electrode 12 on the patient. Such techniques are conventional and well known. The pull tab 36 and the release liner 34 may be composed of any one of a number of materials, such as silicone-coated paper.

Figure 4:
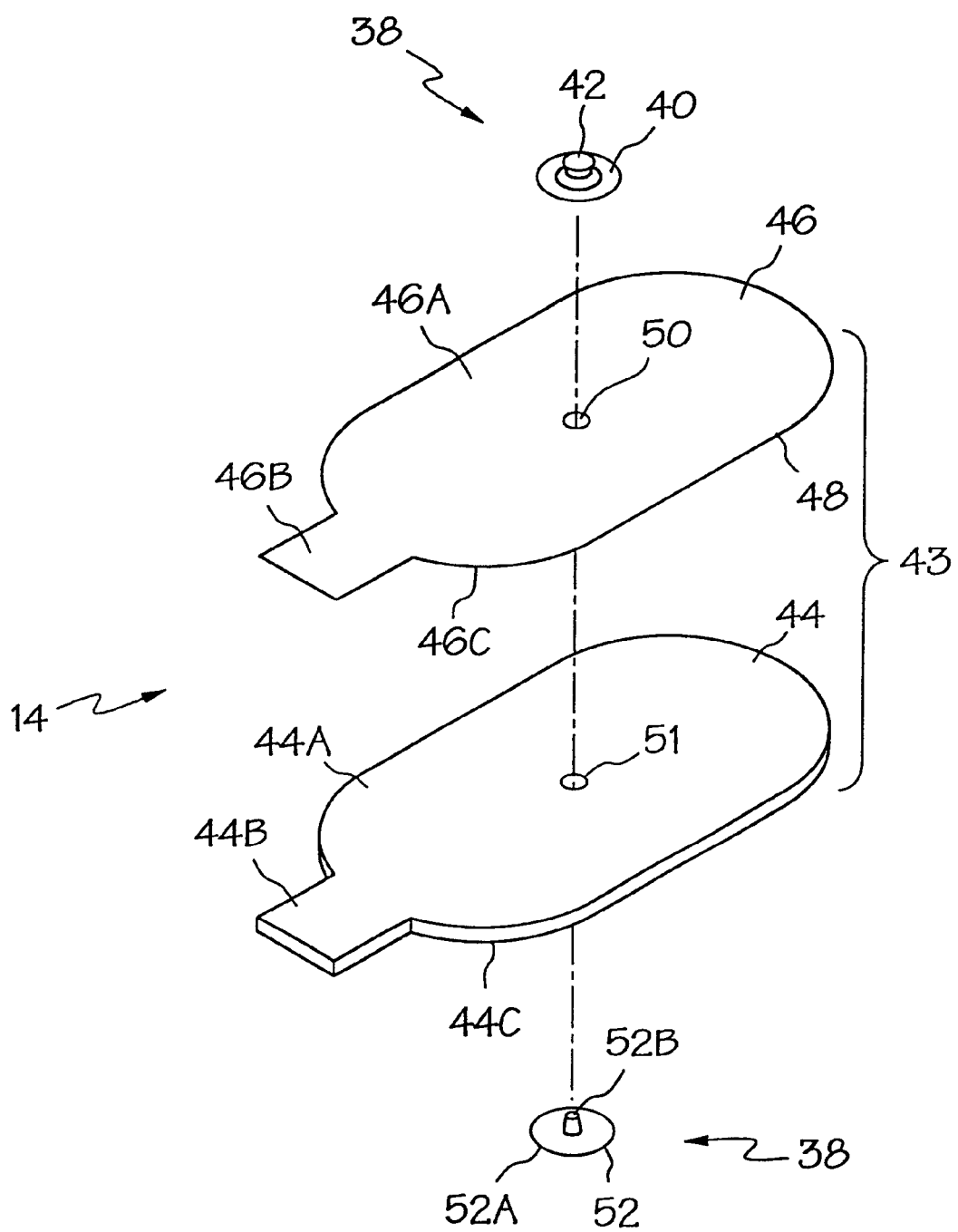
FIG. 4 is an exploded view of the reusable leadwire adapter in accordance with an embodiment of the present invention.

According to an embodiment of the present invention, the reusable leadwire adapter 14 is designed to interface with the standard leadwire connector 16 and the disposable electrode 12 as shown in FIG. 1. The disposable electrode 12 interfaces with the reusable leadwire adapter 14 through the upper surface of the gel layer 18 as described herein. Referring to FIGS. 1 and 4, the reusable leadwire adapter 14 includes a conductive terminal 38 comprising a base portion 40 integrally joined to a stud member 42. The stud member 42 is sized and shaped to snap into any standard leadwire connector 16. The reusable leadwire adapter 14 includes a support layer 43 through which the conductive terminal 38 is coupled. The support layer 43 includes a mounting layer 44 and an optional top layer 46. The top layer 46 includes an adhesive coating 48 to secure the top layer 46 to the mounting layer 44. The top layer 46 has a shape corresponding to the shape of the mounting layer 44. The reusable leadwire adapter 14 may have any shape that is compatible with the patient and the disposable electrode 12. In the illustrated embodiment, the top layer 46 and the mounting layer 44 are oblong shaped with grippable portions 46B and 44B to correspond with the shape of the disposable electrode 12. The grippable portions 46B and 44B are also sized so that the reusable leadwire adapter 14 may be easily grasped with two fingers to facilitate handling and positioning of the electrode 14. It will be appreciated by those skilled in the art that the reusable leadwire adapter 14 and the disposable electrode 12 may have different shapes and still function as intended. In the illustrated embodiment, the mounting layer 44 is composed of a material, such as a polyurethane, which is compatible with the adhesive characteristics of the gel layer 18 while the optional top layer 46 is composed of a material similar to the material used to form the first layer 20. The purpose of the top layer 46 is to provide a printable surface that carries a design which improves the esthetics of the reusable leadwire adapter 14.

The top layer 46 and the mounting layer 44 include correspondingly sized openings 50 and 51, respectively. The opening 50 is located near the center portion of the top layer 46 and the opening 51 is located near the center portion of the mounting layer 44. The base portion 40 of the conductive terminal 38 is positioned on a first or upper surface or side 46A of the top layer 46. The base portion 40 is also wider than the opening 50 and completely covers the opening 50. It should be apparent that the base portion 40 may be positioned on a first or upper surface or side 44A of the mounting layer 44 if the optional top layer 46 is not used. The conductive terminal 38 may be formed of any conductive material. The conductive terminal 38 is preferably formed of a metallic material, such as stainless steel, or is provided with a metallized outer layer, but it can comprise other materials such as conductive carbon interdispersed in a thermoset carbon. It will be appreciated by those skilled in the art that other conductive materials may be used to form the conductive terminal 38.

Further, the reusable electrode adapter 14 comprises a conductive eyelet 52 positioned on a second or lower surface or side 44C of the mounting layer 44. The conductive eyelet 52 has a generally flat surface 52A. In the illustrated embodiment, the gel layer 18 is sized larger than the diameter of the conductive eyelet's lower surface 52A so that the generally flat surface 52A of the conductive eyelet 52 makes complete contact with the gel layer 18. Further, the width of the electrical stabilizing strip 30 is substantially equal to the width of the conductive eyelet 52. In the illustrated embodiment, the conductive eyelet 52 is substantially circular such that the width of the conductive eyelet 52 corresponds to the diameter of the conductive eyelet 52. The conductive eyelet 52 is electrically and mechanically coupled to the base portion 40 of the conductive terminal 38 through the openings 50 and 61. The conductive eyelet 52 includes a stud portion 52B which protrudes through the openings 50 and 51 and securely fastens the conductive terminal 38 to the support layer 43. The conductive eyelet 52 may be friction fitted, riveted or crimped into the conductive terminal 38. An adhesive may also be used to fasten the conductive terminal 38 to the first surface 46A of the top layer 46 and the conductive eyelet 52 to the second surface 44C of the mounting layer 44.

Preferably, the conductive eyelet 52 is formed of a metallic material, such as silver, with a chlorinated outer surface. The conductive eyelet 52 can be formed of solid silver. As discussed previously, however, only a minute amount of silver is needed to yield high quality traces. Lower cost alternatives include nonconductive materials, such as nylon or plastic, that can be made conductive by inclusion of carbon, and plated or coated with at least one particle of silver. It is also possible to use silver plated non-conductive material to yield high quality traces.

While silver is the preferred metallic material, other metals, such as stainless steel or zinc, may also be used. See U.S. Pat. No. 3,976,055, incorporated by reference, for additional types of metals and the manner in which they can be applied. It should be kept in mind that the conductive material selected for this purpose should also be compatible with the electrically conductive gel layer in the disposable electrode. Silver with a chlorinated outer surface is compatible with most electrically conductive gel layers currently used and preferred for long term monitoring applications.

Correspondingly, it is preferable to have a gel layer 18 which is a hydrogel material formed from an aqueous mixture of polyhydric alcohol, an aliphatic diisocyanate-terminated prepolymer, polyethylene oxide-based diamine, and sodium chloride. It should be understood that hydrogels other than those described herein which have the desired properties may be used as the gel layer 18 without departing from the scope of the invention. Preferably, the polyhydric alcohol is selected from the group consisting of polypropylene glycol, polyethylene glycol and glycerine. The resulting hydrogel material is an electrically conductive and highly absorbent material capable of retaining large amounts of fluid, thereby rendering it very moist and soothing. By forming the hydrogel material from the aforementioned aqueous mixture, it remains intact and experiences minimal "dry-out" problems, even over extended storage periods.

Moreover, the hydrogel used to form the gel layer 18 does not adhere or stick to the patient's body, thereby allowing for easy removal of the disposable electrode 12 substantially as a single piece and without adhering to the patient's hair. Additionally, the biocompatibility of the hydrogel is extremely favorable and, therefore, provides a biocompatible, non-irritating, fluid-absorbing, bacterial-protective, cushioning, skin-like media in and over the patient's skin during monitoring.

Those skilled in the art will appreciate that a wide variety of aliphatic diisocyanates may be used in accordance with the invention including but not limited to hexamethylene diisocyanate, isophoronediisocyanate, tetramethylene diisocyanate, and decamethylene diisocyanate. The preferred aliphatic diisocyanate-terminated prepolymer, however, is an isophoronediisocyanate-terminated prepolymer based on polyols containing more than about 40% polyethylene oxide and having an isocyanate content of about 3% by weight. The molecular weight of the isophoronediisocyanate-terminated prepolymer is preferably, from about 1500 to about 8000 and, most preferably, from about 4000 to 5000. The polyethylene oxide-based polyamine is preferably a polyethylene oxide-based diamine having a molecular weight in a range from about 200 to about 6000 and, most preferably about 2000. It is also preferable that the aliphatic diisocynate-terminated prepolymer and the polyethylene oxide-based polyamine have a stoichiometric ratio of about 1:1. Those skilled in the art will appreciate that all of the constituents of the preferred hydrogel material may be readily synthesized or purchased commercially, with neither method preferred over the other.

It has also been found that a more preferred hydrogel material is formed from an aqueous mixture including from about 0% to about 90% by weight polyhydric alcohol; from about 6% to about 60% by weight aliphatic diisocyanate-terminated prepolymer; from about 4% to about 40% by weight polyethylene oxide-based polyamine; up to about 2% by weight sodium chloride; and the balance water. A more preferred hydrogel composition for forming the hydrogel material is formed from a mixture comprising from about 15% to about 30% by weight polypropylene glycol; from about 8% to about 14% by weight isophoronediisocyanate-terminated prepolymer; from about 5% to 10% by weight polyethylene oxide-based diamine; up to about 1% by weight sodium chloride; and the balance water. Most preferably, the hydrogel material is formed from a mixture comprising: (a) from about 16% to 17% by weight polypropylene glycol; (b) from about 10% to 12% by weight isophoronediisocyanate-terminated prepolymer; (c) from about 7% to 9% by weight polyethylene oxide-based diamine; (d) from about 0.5% to 1% by weight sodium chloride; and (e) the balance water.

The gel layer 18 performs numerous functions. First, the gel layer 18 provides the electrical interface to transfer the electrical potentials accurately from the patient's skin to the conductive portion of the biomedical electrode 10. The gel layer 18 also provides an adhesive feature for securing the reusable leadwire adapter 14 to the disposable electrode 12. The polyurethane of the mounting layer 44 is selected so as to provide sufficient adhesive retention with the gel layer 18. The gel layer 18 also performs a self-cleaning function for the reusable leadwire adapter 14 by absorbing dirt and dust on the second surface 44C of the mounting layer 44 without substantially affecting the adhesive quality of the gel layer 18.

The biomedical electrode 10 according to the illustrated embodiment is used as follows. The user snaps the standard leadwire connector 16 to the stud member 42 of the reusable leadwire adapter 14. The disposable electrode 12 is removed from the release liner 34 and placed on the patient's skin. The reusable leadwire adapter 14 is placed on top of the disposable electrode 12 so that conductive eyelet 52 contacts the gel layer 20, and hence, provides an electrical connection to the patient's skin through the opening 22. Alternatively, the reusable leadwire adapter 14 may be placed on top of the disposable electrode 12 first, and then snapped into standard leadwire 16. The order of connection is not critical as long as the conductive eyelet 52 contacts the gel layer 18 which in turn contacts the patient's skin, and the stud member 42 snaps into the standard leadwire connector 16. The reusable leadwire adapter 14 is secured to the disposable electrode 12 through the adhesive interaction of the gel layer 18 and the mounting layer 44. This adhesive interaction is sufficient to keep the biomedical electrode 10 secured in place during long term monitoring and stress testing applications in which the patient is active.

The self-cleaning feature of the gel layer 18 is apparent. After monitoring is concluded, the reusable leadwire adapter 14 is separated from the disposable electrode 12 by simply peeling away at the interface. The disposable electrode 12 is removed from the patient and thrown away. The second surface 44C of the mounting layer 44 of the reusable leadwire adapter 14 is simply wiped clean with a damp cloth, if necessary, and the reusable leadwire adapter 14 is then ready for reuse. Due to the tacky nature of the gel layer 18, much of the dust which may be deposited on surface 44C from time to time will be carried away on the gel layer 18, as well.

The reusable leadwire adapter 14 lasts as long as a standard leadwire connector, i.e. from three months to a year. The disposable electrode 12 contains no metallic material so the cost of manufacturing is reduced. On the other hand, the reusable leadwire adapter 14 contains the relatively expensive metallic materials needed for a high quality trace, and it is reusable. The cost of the relatively expensive metallic materials is spread over a larger number of monitoring events such that the per use cost is less. Further, the disposable electrode 12 and the reusable leadwire adapter 14 are used in the same manner as current monitoring electrodes such that user retraining is not required. The gel layer 18 provides sufficient adhesion for coupling the disposable electrode 12 to the reusable leadwire adapter 14 so that additional, and expensive adhesives are not required. Finally, the reusable leadwire adapter 14 is designed to interface with standard leadwires so that hospitals do not have to buy new leadwires to use the electrodes constructed according to embodiments of the present invention.

Figure 5:
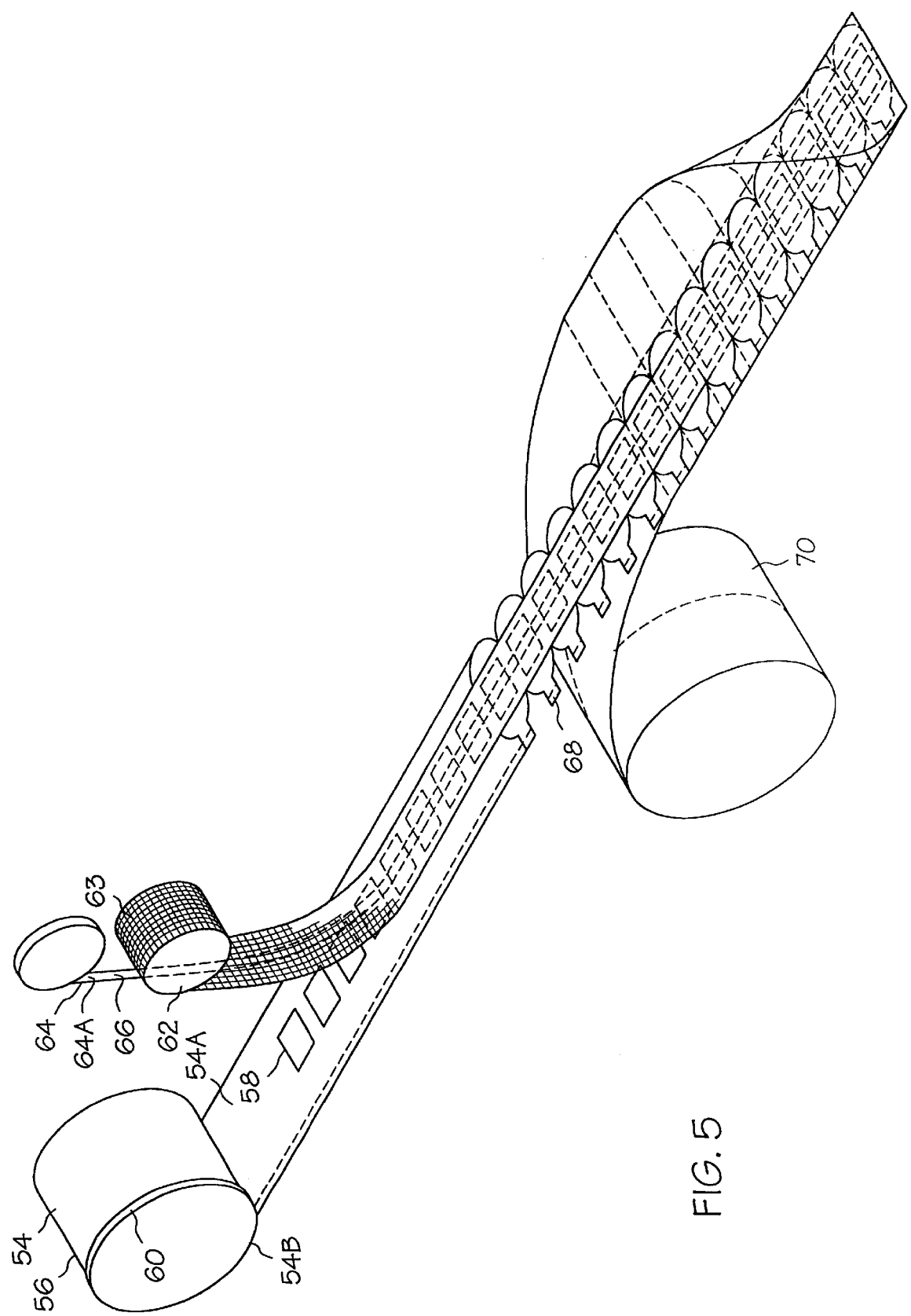
FIG. 5 is an exploded view of the manufacturing process of the disposable electrode in accordance with an embodiment of the present invention.

FIG. 5 illustrates a method for manufacturing the disposable electrode 12. A roll of the first layer 54 is provided having an adhesive 56 applied to a second or lower surface 54B. The adhesive 56 may be applied in conjunction with the formation of the first layer 54 or the adhesive 56 may be applied after the first layer 54 is formed. An opening 58 is formed through the center portion of the first layer 54 at predetermined intervals such that at least one opening 58 is provided for each of the disposable electrodes 12. In the illustrated embodiment, the first layer 54 includes a pull tab portion 60 on the second surface 54B. The pull tab portion 60 may be applied to the first layer 54 as the first layer 54 is formed or as the disposable electrodes 12 are being formed.

An electrically conductive gel web 62 is applied to a first or upper surface 54A of the first layer 54. The electrically conductive gel web 62 is secured or laminated to the first layer 54. As illustrated in FIG. 5, the gel web 62 includes the optional support structure 63 already formed within the gel web 62. It will be appreciated by those skilled in the art that the optional support structure 63 may be added to the gel web 62 as a separate step after the gel web 62 is formed and unrolled as part of the process of forming the disposable electrode 12. As stated above, the material of the first layer 20 or the material of the roll of first layer 54 is of sufficient porosity such that the first layer 54 can be secured or laminated to the gel web 62 without an adhesive.

An electrical stabilizing strip 64 is provided having an adhesive 66 on the surface 64A. The electrical stabilizing strip 64 is applied to the gel web 62 so that the strip 64 is wedged between the first layer 54 and the gel web 62. It will be appreciated by those skilled in the art that the strip 64 may be applied to the gel web 62 through the opening 58 such that the strip 64 is also attached to the second surface 54B of the first layer 54. In the illustrated embodiment, the electrically conductive gel web 62 is applied in the center portion of the first layer 54 while the electrical stabilizing strip 64 is applied to the center portion of the gel web 62.

The resultant combination is then cut to the desired oblong shape with the grippable portion 68. A release liner 70 is applied to the second surface 54B of the first layer 54. A separation cut is made such that the web is turned into individual disposable electrodes 12 and can be easily removed. The release liner 70 is sized so that a portion 70A may be folded over the first surface 54A of the first layer and thereby protect both the first and second surfaces 54A, 54B of the first layer 54. The separation cut may be made before or after the release 70 is folded. The materials described with respect to the disposable electrode 12 are the same materials used in the above manufacturing process.

Having described the invention in detail and by reference to preferred embodiments thereof, it will be apparent that modifications and variations are possible without departing from the scope of the invention which is defined in the appended claims.

What is claimed is:

1. A method of manufacturing disposable electrodes from a web comprising the steps of:

providing a first layer having a first surface and a second surface;

applying an adhesive to said second surface of said first layer;

forming a plurality of openings through said first layer;

applying an electrically conductive gel web to said first surface of said first layer such that said gel web extends over each of said plurality of openings; and, delineating said first layer into a plurality of electrodes such that each of said plurality of electrodes includes at least one of said plurality of openings.

2. The method of claim 1, further comprising a step of cutting said first layer to a predetermined shape.

3. The method of claim 1, further comprising a step of applying a release liner to said first layer.

4. The method of claim 3, wherein said step of applying release liner to said first layer further comprises a step of applying a release liner to said second surface of said first layer and a step of folding said release liner over said first surface of said first layer.

5. The method of claim 1, further comprising a step of making a separation cut through said first layer between said plurality of electrodes.

6. The method of claim 1, further comprising a step of forming a grippable surface on each of said plurality of electrodes.

7. The method of claim 1, further comprising a step of applying an electrical stabilizing strip to said electrically conductive gel web.

8. The method of claim 7, wherein said step of applying an electrical stabilizing strip includes the step of providing an insulating material in said electrical stabilizing strip.

9. The method of claim 8, wherein said step of providing an insulating material in said electrical stabilizing strip includes the step of providing a polyester material in said insulating material.

10. The method of claim 1, wherein said step of applying an electrically conductive gel web includes the step of providing a hydrogel in said electrically conductive gel web.

11. The method of claim 1, wherein said step of applying an electrically conductive gel web includes a step of laminating an electrically conductive gel web to said first surface of said first layer.

12. The method of claim 1, wherein said step of providing an electrically conductive gel web includes the step of providing a support layer disposed within said electrically conductive gel web.

13. The method of claim 1, wherein said first layer is sufficiently porous that said electrically conductive gel web laminates to said first layer without using adhesives.

14. The method of claim 1, further comprising a step of applying a support structure after applying said electrically conductive gel web.

15. The method of claim 1, further comprising a step of applying an electrically stabilizing strip between said first layer and said electrically conductive gel web such that said electrically stabilizing strip aligns with each of said plurality of openings.

16. The method of claim 15, further comprising a step of adhesively securing said electrically stabilizing strip to said electrically conductive gel web.

17. The method of claim 1, further comprising a step of applying an electrically stabilizing strip to said first layer such that said electrically stabilizing strip aligns with each of said plurality of openings and attaches to said first layer on said second surface.

* * * * *

UNITED STATES PATENT AND TRADEMARK OFFICE
CERTIFICATE OF CORRECTION

PATENT NO. : 6,276,054 B1
DATED : August 21, 2001
INVENTOR(S) : Cartmell et al.

It is certified that error appears in the above-identified patent and that said Letters Patent is hereby corrected as shown below:

Column 13,
Line 12, reads as "applying release liner", should read -- applying a release liner --.
Line 14, reads as "applying a release liner", should read -- applying said release liner --.

Signed and Sealed this

Ninth Day of April, 2002

Attest:

JAMES E. ROGAN
*Director of the United States Patent and Trademark Office*

*Attesting Officer*